US008079466B2

(12) United States Patent
Lee et al.

(10) Patent No.: US 8,079,466 B2
(45) Date of Patent: *Dec. 20, 2011

(54) DEVICES FOR STORING AND DISPENSING COMPOSITIONS

(75) Inventors: Robert Lee, Lake Elmo, MN (US); Brian A. Shukla, St. Paul, MN (US); Robert W. Petrich, Woodbury, MN (US); Arno Hohmann, Munich (DE); Marc Peuker, Schondorf (DE); John W. Dubbe, Starnberg (DE)

(73) Assignees: 3M Innovatice Properties Company, St. Paul, MN (US); 3M ESPE AG, Seefeld (DE)

( * ) Notice: Subject to any disclaimer, the term of this patent is extended or adjusted under 35 U.S.C. 154(b) by 36 days.

This patent is subject to a terminal disclaimer.

(21) Appl. No.: 12/052,017

(22) Filed: Mar. 20, 2008

(65) Prior Publication Data

US 2008/0171164 A1 Jul. 17, 2008

Related U.S. Application Data

(62) Division of application No. 11/022,455, filed on Dec. 22, 2004, now Pat. No. 7,374,040.

(51) Int. Cl.
*B65D 25/08* (2006.01)
*B65D 71/00* (2006.01)

(52) U.S. Cl. .................. 206/222; 209/229; 209/219

(58) Field of Classification Search ............ 206/15.3, 206/209, 361, 229, 219, 222, 469, 362.3, 206/210, 63.5; 222/145.1, 145.5, 94; 401/132
See application file for complete search history.

(56) References Cited

U.S. PATENT DOCUMENTS

| 2,898,744 A | * | 8/1959 | Robbins ............................. 62/4 |
| 3,336,669 A | | 8/1967 | Kramer |
| 3,618,751 A | | 11/1971 | Rich ................................. 206/47 |
| 3,659,706 A | * | 5/1972 | Serrell .......................... 206/539 |
| 3,756,389 A | * | 9/1973 | Firth ............................. 206/219 |
| 4,519,499 A | * | 5/1985 | Stone et al. .................... 206/219 |
| 4,880,111 A | * | 11/1989 | Bagwell et al. .............. 206/209.1 |
| 4,911,304 A | * | 3/1990 | Bunin ........................... 206/531 |
| 4,952,068 A | | 8/1990 | Flint |
| 5,001,880 A | * | 3/1991 | Smith ............................. 53/453 |
| 5,549,204 A | * | 8/1996 | Toren ............................ 206/539 |
| 5,558,874 A | * | 9/1996 | Haber et al. ................... 424/402 |
| 5,954,996 A | | 9/1999 | Discko, Jr. |

(Continued)

FOREIGN PATENT DOCUMENTS

DE 37 17 512 A1 12/1987

(Continued)

OTHER PUBLICATIONS

Adpern™ Prompt™ L-Pop™ Self-Etch Adhesive Now with Easier Activation and improved chemistry for higher performance, pp. 1-4, ESPE, 70-2009-3435-7, Copyright 2002.

(Continued)

*Primary Examiner* — David T Fidei (57) ABSTRACT

The present invention is a packaging article that includes a first chamber defined by a sealed connection between a first film and a second film, a second chamber defined by a sealed connection between a third film and a fourth film, where the third film at least partially abuts the second film, and a third chamber defined by a sealed connection between the first film and the fourth film.

8 Claims, 5 Drawing Sheets

U.S. PATENT DOCUMENTS

| | | | |
|---|---|---|---|
| 6,105,761 A | 8/2000 | Peuker et al. | |
| 6,328,159 B1 | 12/2001 | Discko, Jr. | |
| 6,612,769 B2 | 9/2003 | Lee et al. | |
| 6,634,498 B2 | 10/2003 | Kayerød et al. | 206/364 |
| 6,695,515 B1 * | 2/2004 | Fleury | 401/132 |
| 6,779,657 B2 | 8/2004 | Mainwaring et al. | 206/229 |
| 7,243,789 B2 | 7/2007 | Discko, Jr. | 206/229 |
| 7,374,040 B2 * | 5/2008 | Lee et al. | 206/229 |
| 2003/0019883 A1 * | 1/2003 | De Laforcade | 222/1 |
| 2003/0038040 A1 | 2/2003 | Bertl et al. | |
| 2003/0146117 A1 | 8/2003 | Raia et al. | |
| 2004/0065679 A1 | 4/2004 | Peuker et al. | |
| 2005/0150904 A1 | 7/2005 | Suchan et al. | |
| 2006/0118434 A1 * | 6/2006 | Leiner et al. | 206/219 |
| 2006/0131189 A1 | 6/2006 | Lee et al. | |
| 2008/0171164 A1 | 7/2008 | Lee et al. | |

FOREIGN PATENT DOCUMENTS

| | | |
|---|---|---|
| DE | 100 09 622 | 9/2001 |
| WO | WO 00/73146 A2 | 12/2000 |
| WO | WO 02/064444 A2 | 8/2002 |
| WO | WO 2004/041107 | 5/2004 |
| WO | WO 2004/041107 A | 5/2004 |
| WO | 2005/087614 | 9/2005 |

OTHER PUBLICATIONS

U.S. Appl. No. 61/022,859, entitled "Dental Package, and Method of Making the Package," filed Jan. 23, 2008.

Search Report for International Publication No. PCT/US2005/045574.

* cited by examiner

DEVICES FOR STORING AND DISPENSING COMPOSITIONS

CROSS REFERENCE TO RELATED APPLICATIONS

This application is a division of U.S. patent application Ser. No. 11/022,455, filed Dec. 22, 2004, now allowed, now U.S. Pat. No. 7,374,040, which is incorporated herein by reference.

BACKGROUND OF THE INVENTION

The present invention relates to a package for storing and dispensing flowable components. In particular, the present invention relates to a package for storing separate flowable components, and dispensing the flowable components in a substantially simultaneous manner.

A number of liquid and semi-liquid compositions are made from two or more flowable components that are typically not mixed together until immediately prior to use. For example, certain adhesives such as epoxies are sold in packages that initially keep components of the adhesive separated from each other. Whenever such adhesives are needed for use, the components are mixed together and a chemical reaction between the two components begins. After the components are mixed, the composition is applied to the work site before the composition unduly hardens.

A number of packages have been proposed over the years for separately containing and storing components of multiple-component compositions. Examples of commonly-used packages for multiple-component compositions include dual-chamber cartridges, static mixers, and applicator assemblies. However, such packages are not sufficient for dispensing multiple-component compositions in a variety of applications, particularly where only a relatively small amount of composition is needed. In those instances, large portions of the initial flowable components may remain in the cartridge after a sufficient amount has been taken for the work at hand.

Moreover, when packages are used in health care fields such as dentistry, the user must take care to avoid cross-contamination between patients in offices where the composition from a single package is used in multiple procedures among different patients. The issue of cross-contamination can be addressed by proper handling of the dispensing assembly to ensure that disinfection of the cartridge, static mixer, and applicator assembly is accomplished as needed. However, inadequate attention to proper disinfection and handling techniques of the assembly may increase the risk of transferring an infectious disease from one patient to another.

As such, single use packages have been developed for storing and dispensing of multiple-component compositions. Such packages may be formed, for example, by sheets of flexible material having initially separate chambers that receive the components. When the composition is needed, the flexible sheets are squeezed together to decrease the volume in the chambers and direct the components along a path for mixing and dispensing. However, a common issue with such packages is the number of steps required to obtain the multiple-component composition. Generally, the flowable components are required to be dispensed into a series of adjacent chambers, which commonly results in an undesirable backflow of the components into previously dispensed chambers. Backflow reduces the total amount of the available composition, and may potentially offset the relative amounts of the flowable components. Accordingly, there is a need in the industry for packages that store and dispense multiple-component compositions that are efficient to use and easy to manufacture.

BRIEF SUMMARY OF THE INVENTION

The present invention is directed to a packaging article that includes a first chamber defined by a sealed connection between a first film and a second film, a second chamber defined by a sealed connection between a third film and a fourth film, where the third film at least partially abuts the second film, and a third chamber defined by a sealed connection between the first film and the fourth film.

The present invention is further directed to a packaging article that includes a first chamber, a second chamber, a third chamber, and a fourth chamber. The first chamber is defined by a sealed connection between a first film and a second film, where the first chamber has a first cross-sectional area at the second film. The second chamber is defined by a sealed connection between a first film and a second film. The third chamber is defined by a sealed connection between a third film and a fourth film, where the third chamber has a second cross-sectional area at the third film, and where at least about 75% of the first cross-sectional area overlaps the second cross-sectional area. The fourth chamber is defined by a sealed connection between the third film and the fourth film.

The present invention is further directed to a method of making a packaging article. The method includes connecting a first film to a second film, thereby forming a first chamber located between the first film and the second film. A third film is connected to a fourth film, thereby forming a second chamber located between the third film and the fourth film. The first film is connected to the fourth film, thereby forming a third chamber located between the first film and the fourth film.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

Figure 1A:
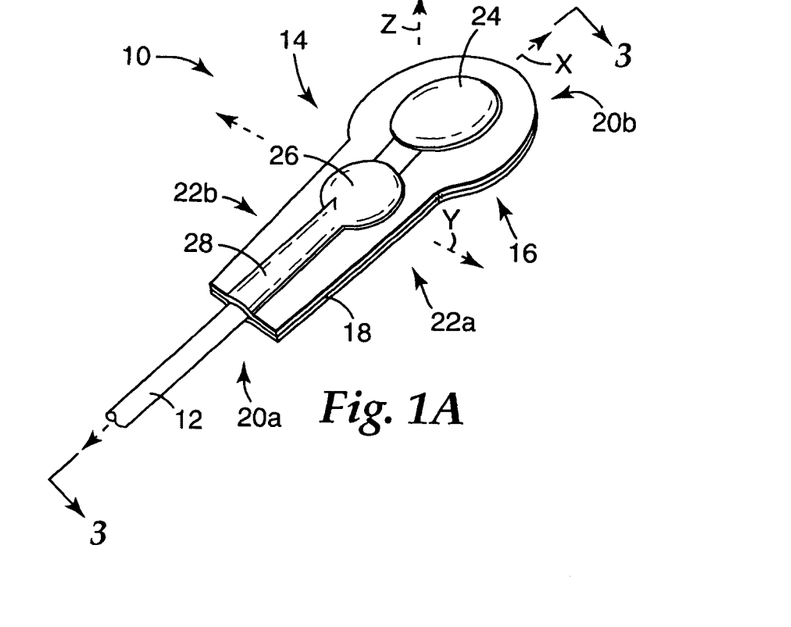
FIG. 1A is a top perspective view of a package of the present invention.
Figure 1B:
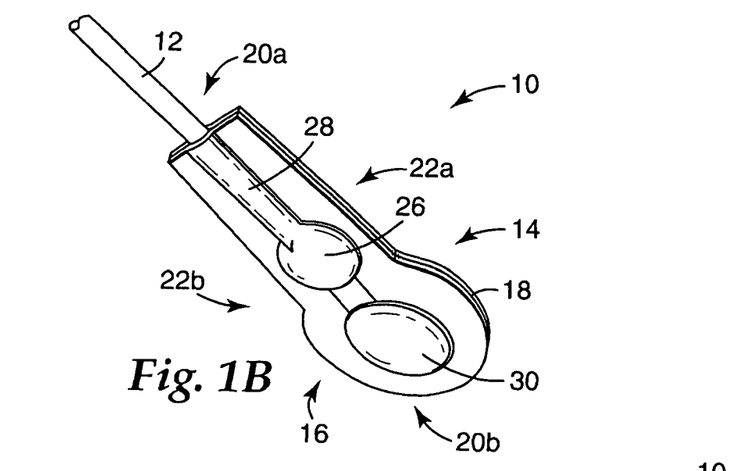
FIG. 1B is a bottom perspective view of the package of the present invention.
Figure 2:
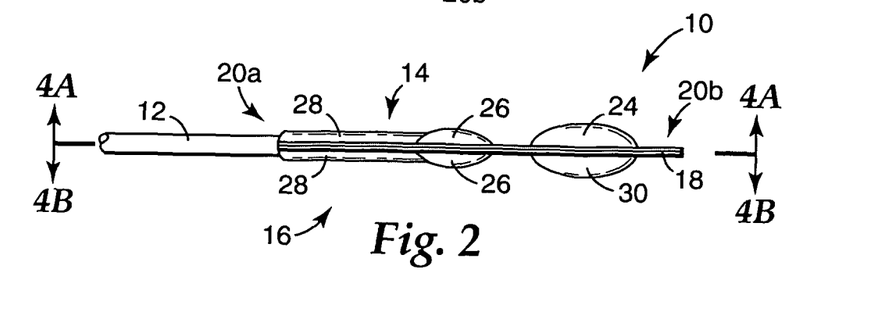
FIG. 2 is a side view of the package of the present invention.

FIGS. 1A, 1B, and 2 are respectively a top perspective view, a bottom perspective view, and a side view of a package 10 of the present invention, in use with a brush 12. The package 10 is a multi-layer device that is capable of dispensing flowable components of a multiple-component composition in a substantially simultaneous manner. This reduces the time required to mix, dispense, and use the composition. As shown in FIG. 1A, the package 10 includes a top film 14 secured above a bottom film 16 at an interface 18. Dimensionally, the package 10 also includes a front end 20a and a rear end 20b relative to a dimension X, and lateral sides 22a and 22b relative to a dimension Y.

Directional orientations are used herein for the sake of clarity, and are not intended to limit the scope of the present invention. Terms such as "front" and "rear", are defined herein as being relative to the dimension X. Terms denoting lateral orientations are defined herein as being relative to the dimension Y. Terms denoting orientations perpendicular to a plane defined by the dimensions X and Y, such as "top", "above", "bottom", and "below", are defined herein as being relative to a dimension Z.

As shown, the top film 14 partially defines a top chamber 24, a mixing chamber 26, and a passageway 28, all of which are located between the top film 14 and the bottom film 16, and are centrally aligned relative to the lateral sides 22a and 22b. The top chamber 24 is located proximate the rear end 20b of the package 10. The passageway 28 is located proximate the front end 20a of the package 10. The mixing chamber 26 is centrally located between the top chamber 24 and the passageway 28.

As shown in FIG. 1B, the bottom film 16 partially defines a bottom chamber 30, the mixing chamber 26, and the passageway 28, where the bottom chamber 30 is also located between the top film 14 and the bottom film 16.

As shown in FIG. 2, the top chamber 24 is disposed above bottom chamber 30. The top chamber 24 and the bottom chamber 30 are separate containers that store flowable components of the multiple-component composition for use during a dispensing process. As discussed below, the top chamber 24 and the bottom chamber 30 are each sealed closed relative to the external environment for storing the flowable components. The package 10 may be used to mix and dispense any of a number of multi-component compositions that are useful for a variety of purposes. For example, the top chamber 24 and the bottom chamber 30 may initially contain flowable components of a two-part epoxy adhesive that are ideally separated from each other until immediately prior to use.

The package 10 is particularly suitable for use with multiple-component dental compositions, because the package 10 can be sized to contain an amount suitable for a single use or for use with a single patient. As such, issues of cross-contamination between patients are avoided. An example of a suitable dental composition is a two-part adhesive material, which may be applied to a surface (e.g., a tooth) with the brush 12. Prior to use, a first part of the adhesive material may be stored in the top chamber 24 and the second part stored in the bottom chamber 30.

The top chamber 24 and the bottom chamber 30 are depicted in FIGS. 1A, 1B, and 2 as generally having circular, dome-like shapes. When used to dispense dental compositions, the top chamber 24 and the bottom chamber 30 may exhibit diameters (along the longitudinal axis X) ranging from about 10 to about 18 millimeters. However, the dimensions of the of the top chamber 24 and the bottom chamber 30 may each vary based on a variety of factors, such as the amounts of the flowable components required. Moreover, the top chamber 24 and the bottom chamber 30 may alternatively exhibit other geometric forms as well.

In contrast to the top chamber 24 and the bottom chamber 30, the mixing chamber 26 is a single chamber defined by both the top film 14 and the bottom film 16. The mixing chamber 26 is connected to both the top chamber 24 and the bottom chamber 30, as discussed below, for receiving the flowable components during the dispensing process.

The passageway 28 is a channel that is also defined by both the top film 14 and the bottom film 16. The passageway 28 is connected to the mixing chamber 26, and provides a path between the mixing chamber 26 and the front end 20a of the package 10. The passageway 28 may also function as a receptacle for the brush 12, where the brush 12 may be a conventional brush for dental applications. The brush 12 may be removably inserted into the passageway 28 to reach the multiple-component composition in the mixing chamber 26. As such, the inner cross section of the passageway 28 is desirably slightly larger than the outer diameter of the brush 12 so that the brush 12 is frictionally retained in the passageway 28, but is still removable.

During a dispensing process, pressure may be simultaneously applied to the top chamber 24 and the bottom chamber 30 in a single step. The pressure may be applied by placing a user's digit on the top chamber 24 and the user's thumb on the bottom chamber 30. The user may then squeeze the top chamber 24 and the bottom chamber 30 together between the digit and thumb. The applied pressure is distributed between the top chamber 24 and the bottom chamber 30, and causes the top chamber 24 and the bottom chamber 30 to collapse in a substantially simultaneous manner. The collapsing reduces the volumes in the top chamber 24 and the bottom chamber 30, which forces the respective flowable components to flow out of the top chamber 24 and bottom chamber 30, and into the mixing chamber 26. The mixing chamber 26 then contains the multiple-component composition, which is accessible by the brush 12 for use. Additional mixing may also be obtained, if desired, by rotating or otherwise moving the brush 12 while the brush 12 extends into the mixing chamber 26.

The package 10 of the present invention allows the flowable components to be dispensed into the mixing chamber 26 in a substantially simultaneous manner. This is due to the vertical stacking of the top chamber 24 and the bottom chamber 30, which allows a single application of pressure to compress both the top chamber 24 and the bottom chamber 30. Therefore, the time required to dispense and mix multiple-component compositions is reduced.

Figure 3:
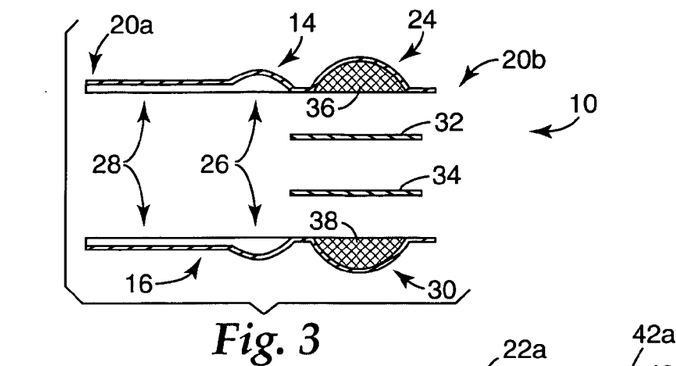
FIG. 3 is an exploded sectional view taken from section 3-3 in FIG. 1A.

FIG. 3 is an exploded sectional view of the package 10 of the present invention, taken from section 3-3 in FIG. 1A (the brush 12 not shown). FIG. 3 further illustrates the working relationship between the top film 14 and the bottom film 16. As discussed above, when the top film 14 and the bottom film 16 are secured together, they combine to define the mixing chamber 26 and the passageway 28. In contrast, however, the top chamber 24 and the bottom chamber 30 are separated from each other by cover films 32 and 34. The top chamber 24 is defined by the top film 14 and the cover film 32, and the bottom chamber 30 is defined by the bottom film 16 and the cover film 34.

Prior to securing the top film 14 and the bottom film 16 together, the top chamber 24 is filled with a flowable component 36, and sealed with the cover film 32. Similarly, prior to securing the top film 14 and the bottom film 16 together, the bottom chamber 30 is filled with a flowable component 38, and sealed with the cover film 34. As such, the flowable components 36 and 38 are separated from each other during storage, and do not mix until dispensed into the mixing chamber 26.

In one embodiment of the present invention, the top film 14 and the bottom film 16 are identical halves of the package 10, where the bottom film 16 is inverted and secured to the top film 14. This reduces the costs of manufacturing the package 10 by decreasing the number of different parts required. The top film 14, the bottom film 16, and the cover films 32 and 34 may be made by any suitable manufacturing technique. For example, the top film 14 and the bottom film 16 may be deep drawn to form indentations for the top chamber 24, the mixing chamber 26, the passageway 28, and the bottom chamber 30.

The top film 14, the bottom film 16, and the cover films 32 and 34 each desirably function as diffusion and light barriers, and each may be made of any suitable material that is compatible with the stored flowable components. Examples of suitable materials for each of the top film 14, the bottom film 16, and the cover films 32 and 34 comprise aluminum, polypropylene, polyethylene, polyethylene terephthalate, and combinations thereof. Moreover, each of the top film 14, the bottom film 16, and the cover films 32 and 34 each may include multiple layers of these materials (and/or other materials). For example, the top film 14 and the bottom film 16 each may include a top layer of polyethylene, an intermediate layer of aluminum film and a bottom layer of polyethylene terephthalate.

Figure 4A:
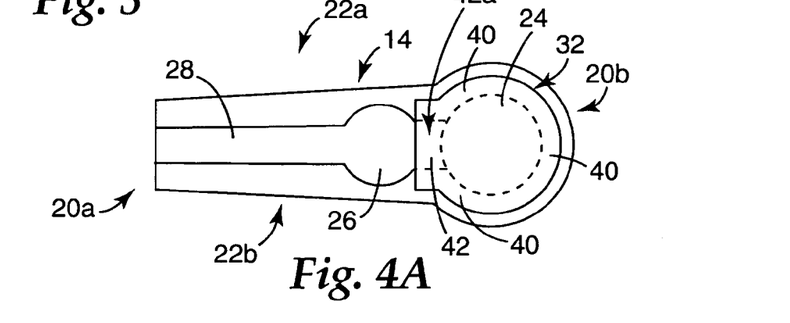
FIG. 4A is a view taken from section 4A-4A in FIG. 2.

FIG. 4A is a view of the top film 14 and the cover film 32, taken from section 4A-4A in FIG. 2 (the brush 12 not shown). As shown in FIG. 4A, the cover film 32 is sealed to the top film 14 proximate the rear portion 20b of the package 10. In the illustrated embodiment, the cover film 32 is sealed to the top film 14 around the entire periphery of the top chamber 24 (e.g., peripheral locations 40). This includes a rupturable seal 42, which connects the top chamber 24 and the mixing chamber 26. The rupturable seal 42 provides a pathway 42a for the flowable component 36 to flow through when forced out of the top chamber 24.

Suitable techniques for sealing the top film 14 and the cover film 32, and for forming the rupturable seal 42 are disclosed in Peuker et al., U.S. Pat. No. 6,105,761, and Lee et al., U.S. Pat. No. 6,612,769, both of which are incorporated herein in their entireties. For example, the top film 14 and the cover film 32 may exhibit a lower interlayer adhesion at the rupturable seal 42, compared to interlayer adhesions at the peripheral locations 40. Thus, prior to the dispensing process, the rupturable seal 42 is sealed closed. However, when the flowable component 36 is subjected to pressure by the collapsing of the top chamber 24, the flowable component 36 delaminates the top film 14 and the cover film 32 at the rupturable seal 42 (i.e., breaks the rupturable seal 42). This allows the flowable component 36 to flow along the pathway 42a into the mixing chamber 26.

Figure 4B:
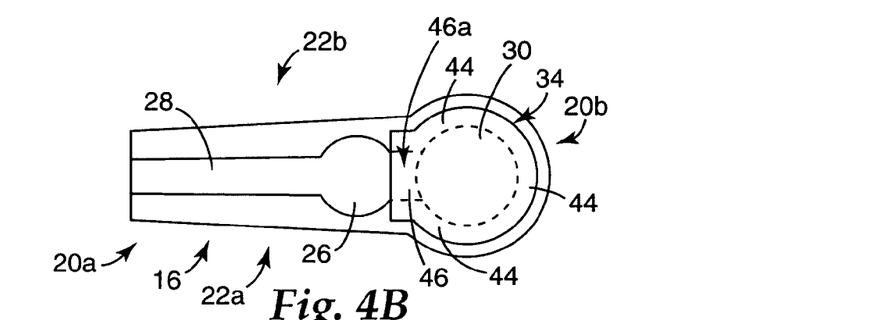
FIG. 4B is a view taken from section 4B-4B in FIG. 2.

FIG. 4B is a view of the bottom film 16 and the cover film 34, taken from section 4B-4B in FIG. 2 (the brush 12 not shown). As shown in FIG. 4B, the cover film 34 is sealed to the bottom film 16 proximate the rear portion 20b of the package 10. In the illustrated embodiment, the cover film 34 is sealed to the bottom film 16 around the entire periphery of the bottom chamber 30 (e.g., peripheral locations 44). This includes a rupturable seal 46, which connects the bottom chamber 30 and the mixing chamber 26, and provides a pathway 46a for the flowable component 38 to flow through when forced out of the bottom chamber 30. Accordingly, when the bottom chamber 30 is collapsed, the flowable component 38 delaminates the bottom film and the cover film 34 at the rupturable seal 46 (i.e., breaks the rupturable seal 46). This allows the flowable component 38 to flow along the pathway 46a into the mixing chamber 26.

The cover films 32 and 34 may exhibit a variety of cross-sectional dimensions. However, as shown in FIGS. 4A and 4B, the cover films 32 and 34 do not seal the mixing chamber 26 or the passageway 28. As discussed above, the mixing chamber 26 and the passageway 28 are each defined by both the top film 14 and the bottom film 16. Therefore, in contrast to the top chamber 24 and the bottom chamber 30, the mixing chamber 26 and the passageway 28 remain exposed until the top film 14 and the bottom film 16 are secured together.

The top film 14 and the bottom film 16 may be secured together with a variety of techniques, such as heat sealing, ultrasonic bonding, pressure bonding, and applying adhesive at the interface 18. For example, an adhesive may be applied to the top film 14 and/or to the cover film 32 to provide interlayer adhesion at the interface 18 between the top film 14 and the bottom film 16, and/or the cover film 34. When the top film 14 and the bottom film 16 are secured together, the top chamber 24 is disposed above the bottom chamber 30. In one embodiment, the top chamber 24 and the bottom chamber 30 are aligned in the longitudinal and lateral directions such that the cover film 32 at least partially abuts the cover film 34. This allows a single application of pressure to compress both the top chamber 24 and the bottom chamber 30 in a substantially simultaneous manner.

In another embodiment, the top chamber 24 and the bottom chamber 30 are aligned in the longitudinal and lateral directions such that at least about 75% of a cross-sectional area of the of the top chamber 24 overlaps a cross-sectional area of the bottom chamber 30. The cross-sectional area of the top chamber 24 is defined herein as an area of the top chamber 24 in a plane defined by the dimensions X and Y, and located at the cover film 32. This is depicted by the illustration of the top chamber 24 in FIG. 4A. Similarly, the cross-sectional area of the bottom chamber 30 is defined herein as an area of the bottom chamber 30 in a plane defined by the dimensions X and Y, and located at the cover film 34. This is depicted by the illustration of the bottom chamber 30 in FIG. 4B. In yet another embodiment, the top chamber 24 and the bottom chamber 30 are aligned in the longitudinal and lateral directions such that at least about 90% of the cross-sectional area of the top chamber 24 overlaps the cross-sectional area of the bottom chamber 30.

When the top film 14 and the bottom film 16 are secured together, the rupturable seal 42 is also disposed above the rupturable seal 46. As such, the flowable components 36 and 38 are substantially unmixed until entering the mixing chamber 26 from the respective rupturable seals 42 and 46 via the pathways 42a and 46a, respectively. In an alternative embodiment, a mixing element (not shown) may be used, which connects the rupturable seals 42 and 46 to the mixing chamber 26 to increase the mixing of the flowable components 36 and 38. Examples of suitable mixing elements include static mixers, which are disclosed in Lee et al., U.S. Pat. No. 6,612,769.

The package 10 of the present invention provides a system for storing and dispensing multiple-component compositions with an efficient dispensing process. As discussed above, during a dispensing process, pressure is applied to the top chamber 24 and the bottom chamber 30 in a substantially simultaneous manner. This causes the flowable components 36 and 38 to respectively break through the rupturable seals 42 and 46, and to flow into the mixing chamber 26. By dispensing the flowable components 36 and 38 in a single step, the package 10 reduces the time required to obtain the multiple-compound composition. Moreover, because a second dispensing step is not required, the dispensing process of the package 10 substantially prevents backflow of the flowable components 36 and 38. Backflow undesirably wastes material and may potentially offset the relative amounts of the flowable components 36 and 38. Finally, because the top film 14 and the bottom film 16 may be identical parts, the package 10 may be manufactured using duplicates of the same parts, which reduces manufacturing time and costs.

Figure 5:
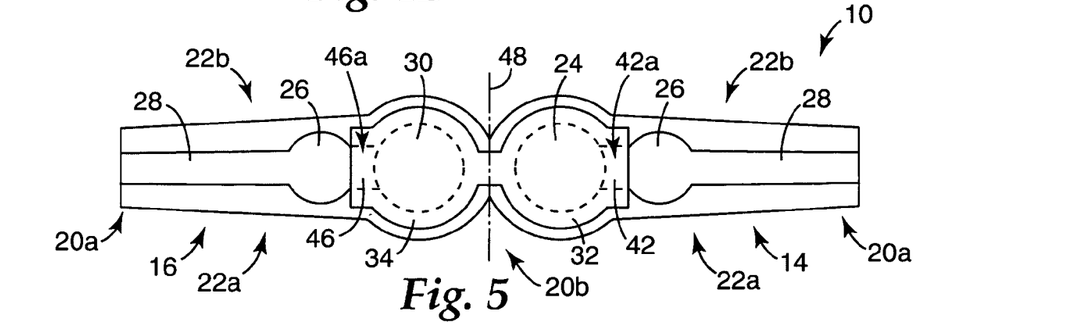
FIG. 5 is a top view of a first alternative construction for the package of the present invention.

FIG. 5 is a top view depicting an alternative method of manufacturing the inventive package 10. The package 10 may be manufactured in a variety of manners to reduce manufacturing time and costs. In the embodiment shown in FIG. 5, the top film 14 and the bottom film 16 are connected at the rear end 20b of the package 10. This allows the top film 14 and the bottom film 16 to be deep drawn initially as a single film (and at the same time). Additionally, the cover films 32 and 34 may also be formed as a single film, as shown. After the top chamber 24 and the bottom chamber 30 are filled with the flowable components 36 and 38, the cover films 32 and 34 are respectively sealed to the top film 14 and the bottom film 16, as discussed above. The top film 14 and the cover film 32 may then be folded at a fold axis 48 to align with the bottom film 16 and the cover film 34.

In another alternative embodiment, the cover films 32 and 34 may be respectively formed as part of the top film 14 and the bottom film 16. In this alternative, the cover films 32 and 34 may extend from the lateral sides 22a and/or 22b proximate the rear end 20b. The cover films 32 and 34 may then be respectively folded over the top film 14 and the bottom film 16, and sealed. These alternative embodiments may also be combined, and used with other conventional techniques to manufacture the package 10 for use as a storage and dispensing product.

FIGS. 6-10 are directed to a package 100, which is a multi-layer device similar to the package 10. However, the package 100 is used for storing and dispensing flowable components in a substantially simultaneous manner, where the flowable components remain separated after being dispensed. An example of suitable flowable components for the package 100 includes a dental adhesive and etchant (or primer-etchant), where the etchant is applied to a surface (e.g., a tooth) prior to the adhesive.

Figure 6:
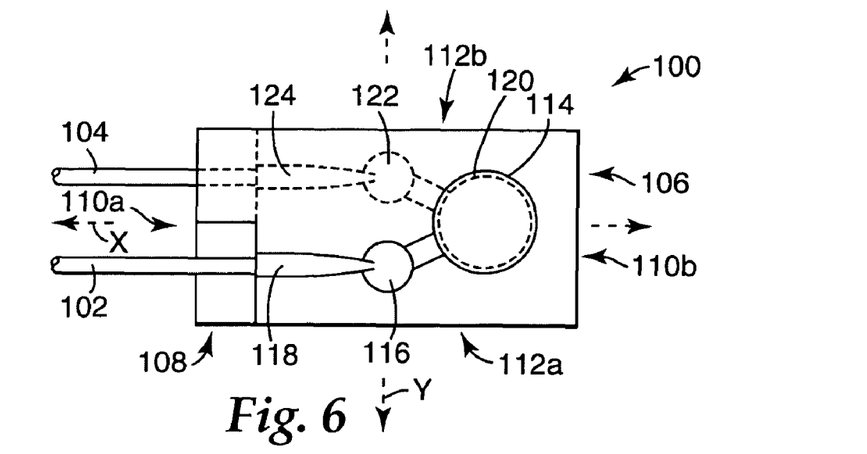
FIG. 6 is a top view of a second alternative package of the present invention.
Figure 7A:
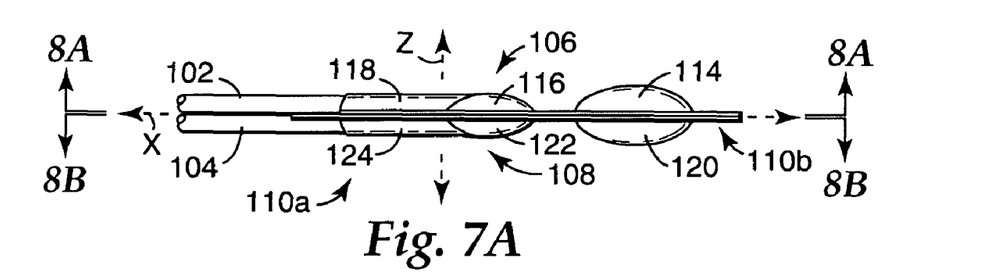
FIG. 7A is a side view of the second alternative package of the present invention.

FIGS. 6 and 7A are a top view and a side view of the package 100, in use with brushes 102 and 104. The brushes 102 and 104 may be conventional brushes for dental applications, similar to the brush 12. The package 100 includes a top film 106 secured above a bottom film 108. The directional orientations discussed above for the package 10 apply in the same manner to the discussion of the package 100. Dimensionally, the package 100 also includes a front end 110a and a rear end 110b, and lateral sides 112a and 112b.

The top film 106 partially defines a top chamber 114, a top receiving chamber 116, and a top passageway 118. Similarly, the bottom film 108 partially defines a bottom chamber 120, a bottom receiving chamber 122, and a bottom passageway 124 (depicted with phantom lines in FIG. 6). The top chamber 114, the top receiving chamber 116, the top passageway 118, the bottom chamber 120, the bottom receiving chamber 122, and the bottom passageway 124 are each located between the top film 106 and the bottom film 108. The top chamber 114 and the bottom chamber 120 are located proximate the rear end 110b of the package 100, with the top chamber 114 being located above the bottom chamber 120. The top passageway 118 is located proximate the front end 110a of the package 100 and the top receiving chamber 116 is centrally located between the top chamber 114 and the top passageway 118. The bottom passageway 124 is also located proximate the front end 110a of the package 100 and the bottom receiving chamber 122 is centrally located between the bottom chamber 120 and the bottom passageway 124.

The top film 106 and the bottom film 108 are preferably identical halves of the package 100, where the bottom film 108 is inverted and secured to the top film 106. In contrast to the package 10, however, where the components are centrally aligned relative to the lateral sides 22a and 22b, the components of the package 100 are not centrally aligned relative to the lateral sides 112a and 112b. The components of the top film 106 are laterally offset from the components of the bottom film 108 (i.e., the top chamber 114, the top receiving chamber 116, and the top passageway 118 are proximate the lateral side 112a, and the bottom chamber 120, the bottom receiving chamber 122, and the bottom passageway 124 are proximate the lateral side 112b). The lateral offsetting is preferred to allow easy access to each of the brushes 102 and 104 without interference of the opposing brush. Nonetheless, the components of the top film 106 and the bottom film 108 may alternatively be centrally aligned if desired.

The top chamber 114 and the bottom chamber 120 are separate containers and function in the same manner as the top chamber 24 and the bottom chamber 30 of the package 10. Pressure may be simultaneously applied to the top chamber 114 and the bottom chamber 120 in a single step, which dispenses flowable compounds in a substantially simultaneous manner. However, the flowable compounds dispensed from the top chamber 114 and the bottom chamber 120 do not flow to a single mixing chamber, as occurs with the package 10. Instead, the flowable compound dispensed from the top chamber 114 flows to the top receiving chamber 116, and the flowable compound dispensed from the bottom chamber 120 flows to the bottom receiving chamber 122. The flowable compounds located in the top receiving chamber 116 and the bottom receiving chamber 116 may then be respectively obtained with the brushes 102 and 104.

Figure 7B:
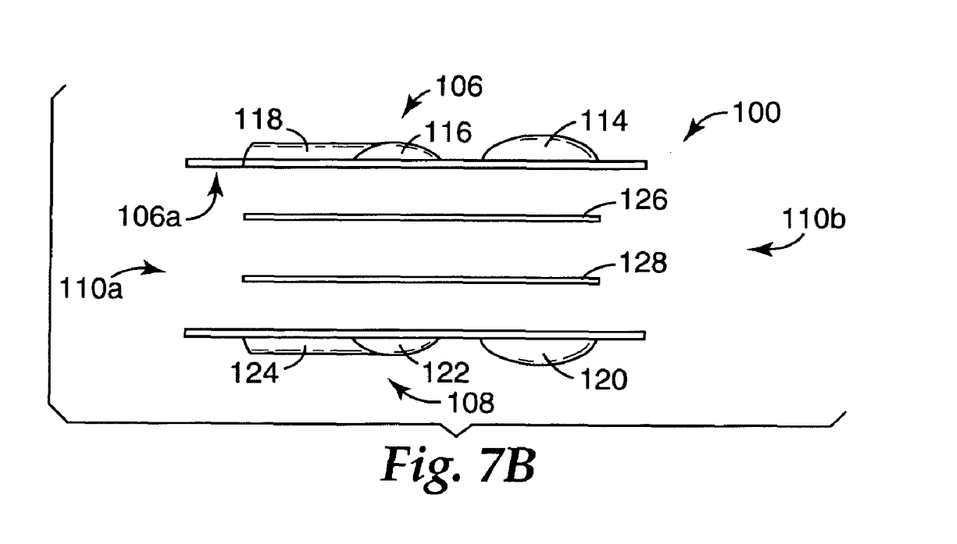
FIG. 7B is an exploded side view of the second alternative package of the present invention.
Figure 8A:
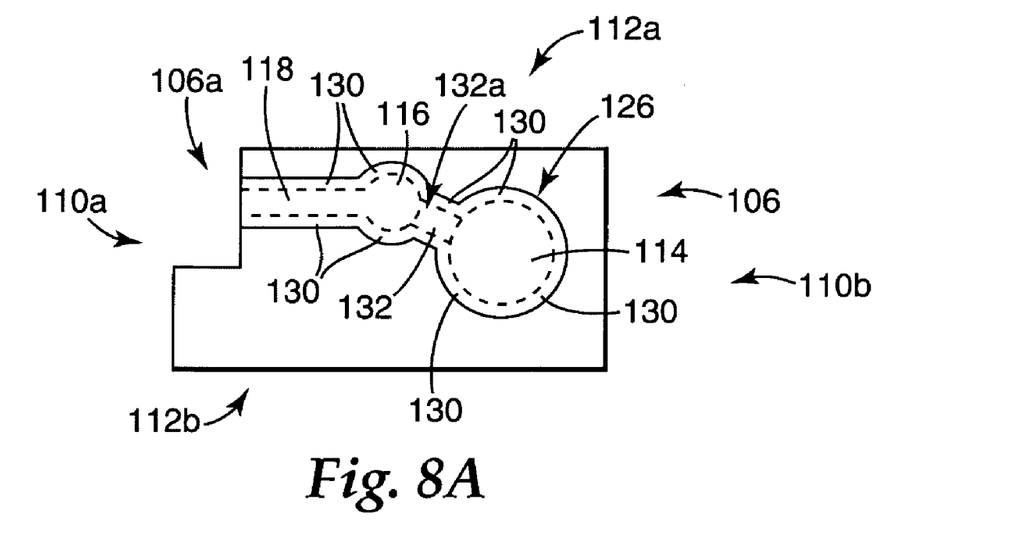
FIG. 8A is a view taken from section 8A-8A in FIG. 7A.

FIG. 7B is an exploded side view of the package 100 and depicts the top film 106 and the bottom film 108 in use with cover films 126 and 128. FIG. 8A is a view of the top film 106, taken from section 8A-8A in FIG. 7A (the brush 102 not shown), and depicts the top film 106 in use with the cover film 126. Similarly, FIG. 8B is a view of the bottom film 108, taken from section 8B-8B in FIG. 7A (the brush 104 not shown), and depicts the bottom film 108 in use with the cover film 128.

As shown in FIGS. 7B and 8A, the cover film 126 is sealed to the top film 106 in the same manner as discussed above for the cover film 32 and the top film 14 of the package 10. However, in addition to sealing the top chamber 114, the cover film 126 also seals the top receiving chamber 116 and the top passageway 118. As such, the cover film 126 is sealed to the top film 106 around the entire periphery of the top chamber 114, the top receiving chamber 116, and the top passageway 118 (e.g., peripheral locations 130). This includes a rupturable seal 132, which connects the top chamber 114 and the top receiving chamber 116, and functions in the same manner as discussed above for the rupturable seal 42 of the package 10 (to define a pathway 132a between the top chamber 114 and the top receiving chamber 116). Accordingly, the top chamber 114, the top receiving chamber 116, and the top passageway 118 are each defined by both the top film 106 and the cover film 126.

Figure 8B:
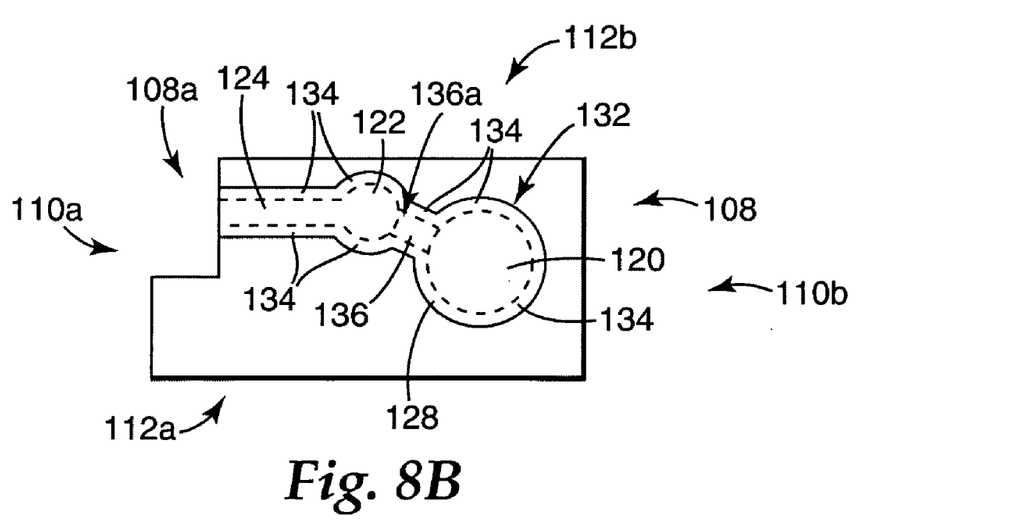
FIG. 8B is a view taken from section 8B-8B in FIG. 7A.

As shown in FIGS. 7B and 8B, the cover film 128 is sealed to the bottom film 108 in the same manner as the cover film 126. As such, the cover film 128 is sealed to the bottom film 108 around the entire periphery of the bottom chamber 120, the bottom receiving chamber 122, and the bottom passageway 124 (e.g., peripheral locations 134). This includes a rupturable seal 136, which connects the bottom chamber 120 and the bottom receiving chamber 122, and functions in the same manner as discussed above for the rupturable seal 136 (to define a pathway 136a between the bottom chamber 120 and the bottom receiving chamber 122). Accordingly, the bottom chamber 120, the bottom receiving chamber 122, and the bottom passageway 124 are each defined by both the bottom film 108 and the cover film 128.

As further shown in FIGS. 8A and 8B, removed corner segments 106a and 108a, proximate the front end 110a of the package 100, may be respectively omitted from the top film 106 and the bottom film 108. As such, the bottom film 108 is visible through the removed corner segment 106a from a vantage point above the package 100 (as shown in FIG. 6), and the top film 106 is visible through the removed corner segment 108a from a vantage point below the package 100. The removed corner segments 106a and 106b provide easier openings for inserting the brushes 102 and 104.

To distinguish the different flowable compounds used with the package 100, the brushes 102 and 104 may exhibit different colors or shapes, or have distinguishing markings. This will allow a user to readily differentiate between the flowable compounds during use.

Suitable materials for the top film 106, the bottom film 108, and the cover films 126 and 132 include the same suitable materials as discussed above for the package 10. Additionally, the cover films 126 and 132 may exhibit a variety of cross-sectional dimensions. For example, the cover films 126 and 132 may alternatively be the same size as the top film 106 and bottom film 108.

The top film 106 and the bottom film 108 may be secured together with a variety of techniques, such as heat sealing, ultrasonic bonding, pressure bonding, and applying adhesive. For example, an adhesive may be applied to the top film 106 and the cover film 126 to provide interlayer adhesion between the top film 106 and the bottom film 108. When the top film 106 and the bottom film 108 are secured together, the top chamber 114 is disposed above the bottom chamber 120. Preferably, the top chamber 114 and the bottom chamber 120 are aligned in the longitudinal and lateral directions such that the cover film 126 at least partially abuts the cover film 128. This allows a single application of pressure to compress both the top chamber 114 and the bottom chamber 120 in a substantially simultaneous manner.

In another embodiment, the top chamber 114 and the bottom chamber 120 are aligned in the longitudinal and lateral directions such that at least about 75% of a cross-sectional area of the of the top chamber 114 overlaps a cross-sectional area of the bottom chamber 120. The cross-sectional area of the top chamber 114 is defined herein as an area of the top chamber 114 in a plane defined by the dimensions X and Y, and located at the cover film 126. This is depicted by the illustration of the top chamber 114 in FIG. 8A. Similarly, the cross-sectional area of the bottom chamber 120 is defined herein as an area of the bottom chamber 120 in a plane defined by the dimensions X and Y, and located at the cover film 128. This is depicted by the illustration of the bottom chamber 120 in FIG. 8B. In yet another embodiment, the top chamber 114 and the bottom chamber 120 are aligned in the longitudinal and lateral directions such that at least about 90% of the cross-sectional area of the of the top chamber 114 overlaps the cross-sectional area of the bottom chamber 120.

During a dispensing process, pressure may be simultaneously applied to the top chamber 114 and the bottom chamber 120 in a single step, as discussed above for the package 10. The applied pressure is distributed between the top chamber 114 and the bottom chamber 120, and causes the top chamber 114 and the bottom chamber 120 to collapse in a substantially simultaneous manner. The collapsing reduces the volumes in the top chamber 114 and the bottom chamber 120, which forces the respective flowable components to flow out of the top chamber 114 and bottom chamber 120. With respect to the top chamber 114, the flowable component breaks the rupturable seal 132 and flows along the pathway 132a into the top receiving chamber 116. The flowable component is then readily accessible with the brush 102 through the top passageway 118. With respect to the bottom chamber 120, the flowable component breaks the rupturable seal 136 and flows along the pathway 136a into the bottom receiving chamber 122. The flowable component is then readily accessible with the brush 104 through the bottom passageway 124.

Figure 9:
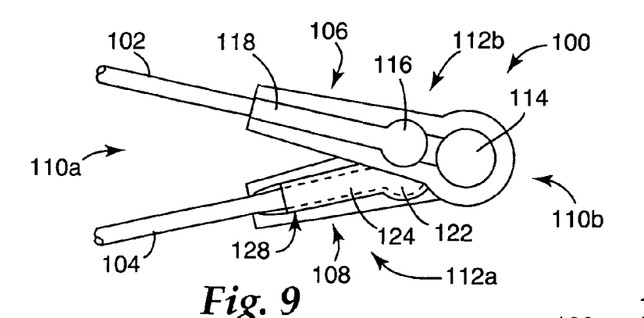
FIG. 9 is a top view of a second embodiment of the second alternative package of the present invention.
Figure 10:
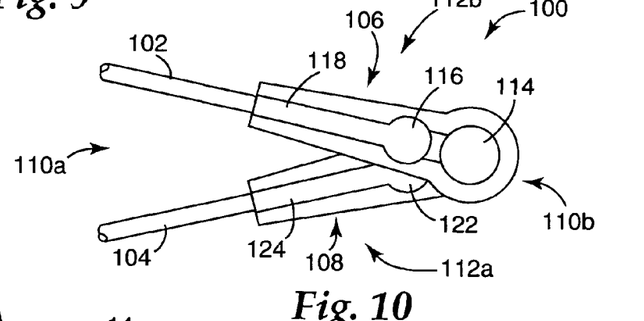
FIG. 10 is a top view of a third embodiment of the second alternative package of the present invention.

FIGS. 9 and 10 are top views of the inventive package 100, depicting alternative shapes and orientations for the top film 106 and the bottom film 108. As shown in FIG. 9, the top film 106 and the bottom film 108 exhibit similar dimensions to the top film 14 and the bottom film 16 of the package 10. Additionally, the top film 106 and the bottom film 108 are oriented at an angle to each other. This increases the accessibility of the brushes 102 and 104. Suitable angles between the top film 106 and the bottom film 108 may vary as individual needs may require.

FIG. 10 provides another alternative arrangement for the package 100, where the bottom film 108 is not inverted relative to the top film 106. As such, the top film 106 is located above the bottom film 108, but both the top film 106 and the bottom film 108 are oriented in an upward direction. The bottom chamber 120 (not shown in FIGS. 9 and 10), the bottom receiving chamber 122, and the bottom passageway 124 likewise extend upward in the same direction as the top chamber 114, the top receiving chamber 116, and the top passageway 118. In this situation, the top film 106 and the cover film 126 (not shown in FIG. 10) are secured to the bottom film 108 at the bottom chamber 120. Pressure is applied to the top chamber 114 and the cover film 128 (not shown in FIG. 10) above the bottom chamber 120 to dispense flowable components from the top chamber 114 and the bottom chamber 120.

Another alternative arrangement for the package 10 includes inverting the package 100 shown in FIG. 10 such that the top film 106 and the bottom film 108 face downward and the cover films 126 and 128 face upward (the relative orientations of the top film 106 and the bottom film 108 remain the same as shown in FIG. 10). This may provide for an easier use of the package 100 with the brushes 102 and 104.

In other embodiments of the present invention, the top passageway 118 may be exposed at the top film 106 and/or the cover film 126. Similarly, the bottom passageway 124 may be exposed at the bottom film 108 and/or the cover film 128. This further increases the convenience of dispensing material from the package 100 with the brushes 102 and 104. For example, with respect to the package 100 shown in FIG. 9, the upper portion of the top passageway 118 is defined by the top film 106 and the upper portion of the bottom passageway 124 is defined by the cover film 128. Thus, in one embodiment, the upper portion of the top passageway 118 may be exposed (i.e., not covered by the top film 106) for easy access with the brush 102. Similarly, the upper portion of the bottom passageway 124 may be exposed (i.e., not covered by the cover sheet 128) for easy access with the brush 104.

With respect to the package 100 shown in FIG. 10, the upper portion of the top passageway 118 is defined by the top film 106 and the upper portion of the bottom passageway 124 is defined by the bottom film 108. Thus, in another embodiment of the present invention, the top film 106 does not cover the top passageway 118 and the bottom film 108 does not cover the bottom passageway 124. This also allows the top passageway 118 and the bottom passageway 124 to be exposed for easy access with the brushes 102 and 104, respectively.

In other embodiments of the present invention, the cover films 126 and 128 may be deep drawn to define trays for dispensing the flowable components, and to prevent the flowable materials from spilling from the package 100 during the dispensing process. This is particularly suitable with the above-discussed embodiments where the top passageway 118 and/or the bottom passageway 124 are exposed.

In further embodiments of the present invention, the packages 10 and 100 may include a plurality of sequential mixing/receiving chambers, such as disclosed in Peuker et al., U.S. Pat. No. 6,105,761. This allows the mixing of multiple flowable components in a sequential manner. Moreover, the subsequent chambers may also include subsequent rupturable seals similar to the rupturable seals 42, 46, 132, and 136. In such embodiments, the subsequent rupturable seals may also be broken by activation of the chambers containing the flowable components (e.g., the chambers 114 and 120). This is particularly suitable where the subsequent chambers have smaller volumes than the preceding chambers. When the flowable components are forced into the smaller chambers, the pressure exerted breaks the subsequent rupturable seals as well. This forces the flowable components further along the sequential chain of mixing/receiving chambers.

Figure 11:
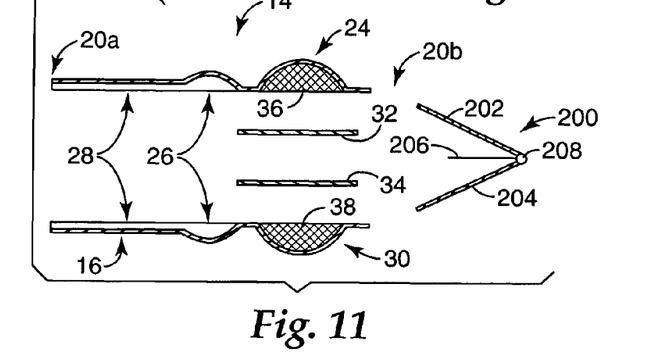
FIG. 11 is an exploded sectional view of a package of the present invention, aligned for assembly with a dispensing device.

The various packages 10 and 100 of the present invention may also be used with dispensing devices, such as clamps, which apply pressure to the top and bottom chambers (i.e., the top chambers 24 and 114 and the bottom chambers 30 and 120). FIG. 11 is a sectional view of the package 10 aligned for assembly with a clamp 200, which is an example of a suitable dispensing device. As shown in FIG. 11, the clamp 200 includes a top plate 202, a bottom plate 204, and an extension member 206, all of which are connected to a hinge 208. The top plate 202 and the bottom plate 204 are capable of moving axially around the hinge 208 relative to each other to open and close the clamp 200. The extension member 206 is a thin-film member that extends from the hinge 208, and may be inserted between the top film 14 and the bottom film 16, when the top film 14 and the bottom film 16 are secured together. In this situation, the clamp 200 is a permanent fixture to the package 10.

Figure 12:
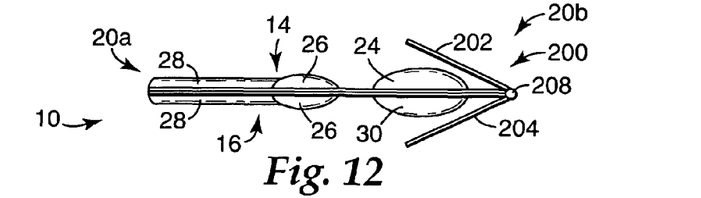
FIG. 12 is a side view of an assembled package of FIG. 11 in use with the dispensing device.

FIG. 12 is a side view of the package 10 in use with the clamp 200. During the dispensing process, a user may apply pressure to the top plate 202 and the bottom plate 204. This simultaneously applies pressure to the top chamber 24 and the bottom chamber 30. Preferably, the top plate 202 and the bottom plate 204 are made of rigid materials to disperse the applied pressure over even surfaces. The clamp 200 may also include a locking arm or other suitable fastener means to secure the clamp 200 in a closed position (with the top plate 202 and the bottom plate 204 aligned generally parallel) after the dispensing process is completed.

The packages 10 and 100 of the present invention are devices for storing multiple flowable components together for use (yet separated), and for mixing and dispensing those multiple flowable components in a substantially simultaneous manner. This reduces the time required to mix, dispense, and use the flowable components. Additionally, the packages 10 and 100 are easy to produce, which reduces manufacturing costs and time. Although the present invention has been described with reference to preferred embodiments, workers skilled in the art will recognize that changes may be made in form and detail without departing from the spirit and scope of the invention.

The invention claimed is:

1. A packaging article for storing and dispensing flowable components, comprising:
   a first chamber defined by a sealed connection between a first film and a second film, wherein the first chamber has a first cross-sectional area at the second film;
   a second chamber defined by a sealed connection between the first film and the second film, wherein the second chamber is connected to the first chamber by a first rupturable seal;
   a third chamber defined by a sealed connection between a third film and a fourth film, wherein the third chamber has a second cross-sectional area at the third film, and wherein at least about 75% of the first cross-sectional area overlaps the second cross-sectional area; and
   a fourth chamber defined by a sealed connection between the third film and the fourth film, wherein the fourth chamber is connected to the third chamber by a second rupturable seal.

2. The packaging article of claim 1, wherein at least about 90% of the first cross-sectional area overlaps the second cross-sectional area.

3. The packaging article of claim 1, and further comprising:
   a first passageway that connects the second chamber to an exterior portion of the packaging article, wherein the first passageway is defined by the sealed connection between the first film and the second film; and
   a second passageway that connects the fourth chamber to an exterior portion of the packaging article, wherein the second passageway is defined by the sealed connection between the third film and the fourth film.

4. The packaging article of claim 3, wherein the first passageway is not parallel to the second passageway.

5. The packaging article of claim 1, wherein the first film and the fourth film are each made from a material selected from a group consisting of aluminum, polypropylene, polyethylene, polyethylene terephthalate, and combinations thereof.

6. The packaging article of claim 1, wherein the first chamber contains a first flowable component and the third chamber contains a second flowable component, and wherein an application of pressure to the first chamber and the third chamber dispenses the first flowable component and the second flowable component in a substantially simultaneous manner.

7. The packaging article of claim 6, wherein the first flowable component is dispensed into the second chamber and the second flowable component is dispensed into the fourth chamber.

8. The packaging article of claim 1, and further comprising a dispensing device, wherein the dispensing device comprises a member that is disposed between the first film and the fourth film.

* * * * *

UNITED STATES PATENT AND TRADEMARK OFFICE
CERTIFICATE OF CORRECTION

| | | |
|---|---|---|
| PATENT NO. | : 8,079,466 B2 | |
| APPLICATION NO. | : 12/052017 | |
| DATED | : December 20, 2011 | |
| INVENTOR(S) | : Robert Lee | |

It is certified that error appears in the above-identified patent and that said Letters Patent is hereby corrected as shown below:

On the Title Page, Item [73], Assignees, delete "Innovatice" and insert --Innovative--, therefor.

On the Title Page, Item [56], Other Publications, delete "Adpern™" and insert --Adper™--, therefor.

Column 4
Line 11, delete "of the of the" and insert -- of the --, therefor.

Column 6
Line 42, delete "of the of the" and insert -- of the --, therefor.

Column 9
Line 59, delete "of the of the" and insert -- of the --, therefor.

Column 10
Line 5, delete "of the of the" and insert -- of the --, therefor.

Signed and Sealed this
Twenty-sixth Day of June, 2012

David J. Kappos
*Director of the United States Patent and Trademark Office*